(12) United States Patent
Kéri et al.

(10) Patent No.: US 6,689,813 B2
(45) Date of Patent: Feb. 10, 2004

(54) PROCESS FOR THE PREPARATION OF PHARMACEUTICAL COMPOSITIONS POSSESSING NEUROGENIC OR NON-NEUROGENIC ANTI-INFLAMMATORY AS WELL AS ANALGETIC EFFECTS

(75) Inventors: György Kéri, Budapest (HU); János Szolcsányi, Pécs (HU); Erika Pintér, Pécs (HU); Zsuzsanna Helyes, Pécs (HU); Judit Érchegyi, Budapest (HU); Anikó Horváth, Budapest (HU); Judith Horváth, Pécs (HU); István Teplán, Budapest (HU); László Őrfi, Budapest (HU)

(73) Assignee: Biostatin Gyogyszerkutato-Fejleszto kft., Budapest (HU)

( * ) Notice: Subject to any disclaimer, the term of this patent is extended or adjusted under 35 U.S.C. 154(b) by 231 days.

(21) Appl. No.: 09/754,598

(22) Filed: Jan. 5, 2001

(65) Prior Publication Data

US 2001/0009899 A1 Jul. 26, 2001

Related U.S. Application Data

(62) Division of application No. 09/296,626, filed on Apr. 23, 1999, now abandoned.

(30) Foreign Application Priority Data

Apr. 27, 1998 (HU) ............................................. 9800970

(51) Int. Cl.$^7$ ..................... A61K 31/195; C07C 251/72
(52) U.S. Cl. .................... 514/565; 514/2; 514/632; 564/251; 570/113
(58) Field of Search ................ 514/565, 632, 514/2; 564/251; 570/113

(56) References Cited

U.S. PATENT DOCUMENTS 3,894,083 A  *  7/1975  Hofen et al.
5,888,765 A  *  3/1999  Patterson et al. .......... 435/69.1

FOREIGN PATENT DOCUMENTS

WO       WO 95/19169      *   7/1995

* cited by examiner

Primary Examiner—Brenda Brumback
Assistant Examiner—Anish Gupta
(74) Attorney, Agent, or Firm—Keil & Weinkauf (57) ABSTRACT

The invention relates to the use of peptide amides of formula (I)

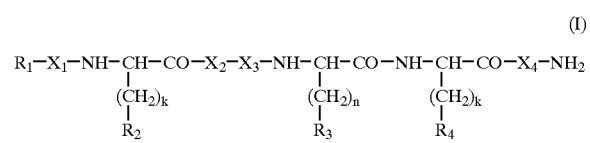

and phenylamino-oxoacetic acid derivatives of formula (II)

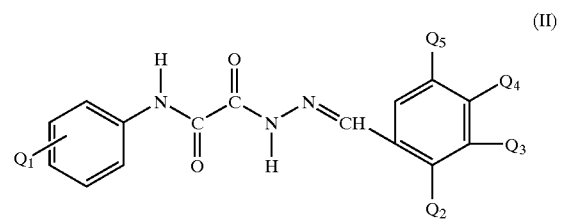

as well as the salts of the above compounds as active substances for the preparation of pharmaceutical compositions possessing neurogenic and non-neurogenic antiinflammatory as well as analgetic effects. In the above formulae, the most important meanings of the substituents are as follows:

$X_1$ means an aromatic D-amino acid group;

$X_2$ stands for an aromatic amino acid group or a derivative thereof ring-substituted by hydroxyl group;

$X_3$ means aromatic D-amino acid group;

$X_4$ means threonyl or tryptophyl group;

k is 0, 1, 2 or 3;

n is 0, 3 or 4;

$R_1$ stands for hydrogen or $CH_3$—CO— group, wherein $A_2$ is $C_{1-4}$ alkyl group;

$R_2$ means hydrogen, phenyl or carbonyl group;

$R_3$ represents hydrogen, amino or $CF_3$—CO—NH— group, $R_4$ stands for hydrogen, phenyl or amino group; or $Q_1$ means hydrogen, halogen, hydroxyl, nitro, amino, $C_{1-4}$ alkyl or alkoxy group;

$Q_2$ stands for hydrogen, halogen, hydroxyl or nitro group;

$Q_3$ represents hydrogen, halogen, hydroxyl, nitro, $CF_3$, $C_{1-4}$ alkyl or alkoxy group;

$Q_4$ and $Q_5$ each represents hydrogen, hydroxyl group, halogen, nitro group, —$CF_3$ group, $C_{1-4}$ alkyl or $C_{1-4}$ alkoxy group; or $C_{1-3}$ dialkylamino group.

5 Claims, 7 Drawing Sheets

PROCESS FOR THE PREPARATION OF PHARMACEUTICAL COMPOSITIONS POSSESSING NEUROGENIC OR NON-NEUROGENIC ANTI-INFLAMMATORY AS WELL AS ANALGETIC EFFECTS

This is a Divisional application of application Ser. No. 09/296,626, filed on Apr. 23, 1999 now abandoned.

BACKGROUND OF THE INVENTION

The invention relates to the use of heptapeptide somatostatin derivatives and peptidomimetics selected therefrom by computerized artificial intelligence software on the basis of chemical similarity for the preparation of pharmaceutical compositions with neurogenic or non-neurogenic anti-inflammatory as well as analgetic effects.

It is known that somatostatin, a tetradecapeptide occurring in the nature and its synthetic analogues inhibit the release of the growth hormone and in addition, they inhibit or control, respectively, a number of other endocrine secretions (e.g. glucagon, insulin, gastrin, prolactin, secretin, cholecystokinin) and cellular functions, too [Reichlin, D.: Somatostatin. N. Engl. J. Med., 309, 1495–1501 (1983)]. It is also known from the literature that, simultaneously with the above endocrine effects, somatostatin and a significant number of its known analogues exhibit also a rather strong inhibitory effect on the cellular growth [Schally, A. V.: Cancer Res. 48, 6977–6985 (1988); U.S. Pat. No. 4,650,787; European patent specifications Nos. 0,215,171 and 0,175,644]. The therapeutical utilization of both the natural hormone and the above analogues is significantly limited by their broad spectrum of activity. Thus, the treatment of various clinical pictures could be considerably improved by selectively acting analogues.

It is also known that compounds of formula (I)

(I)

represent the single group of selectively acting somatostatin peptide analogues. These compounds very strongly inhibit the division of tumorous cells both under in vitro and in vivo conditions but do not show the endocrine effects of somatostatin or other known peptide analogues [Kéri, Gy.: Biochem. Res. Comm. 191, 681–687 (1993); U.S. Pat. No. 5,480,870].

Furthermore, it is known that certain compounds of low molecular weight, namely the so-called "peptidomimetics" carrying functional groups characteristic of a given peptide are capable to undergo an interaction with the peptide receptors and thereby to exert a biological action similar to that of the peptide. The compounds of formula (II)

(II)

are known to strongly inhibit the division of tumour cells similarly to somatostatin analogues (Hungarian patent specification No. 214,061).

It is also known that all inflammatory processes occurring in the organism include more or less neurogenic components. An outstanding importance is attributed to the neurogenic inflammation in the pathomechanism of the following diseases:

a) Inflammations of chiefly allergic origin in the mucous membranes of airways: rhinitis, bronchitis and bronchial asthma;

b) arthritises;

c) allergic conjuctivitis, urticaria;

d) inflammations of the gastrointestinal system, colitis;

e) psoriasis.

At present, no drug is known which could reliably inhibit the neurogenic inflammations, thereby providing the possibility of an efficient treatment of the above pathological pictures. There have been carried out for ages investigations connected with the classic non-steroidal anti-inflammatory drugs but none of the investigated sodium salicylate (250 mg/kg i.v.), amidopyridine (200 mg/kg p.o.), phenylbutazone (100 mg/kg i.v.), flufenamic acid (20 mg/kg i.v.), or indomethacin (10 mg/kg p.o.) exhibited any significant inhibitory effect. Steroids inhibit the neurogenic inflammation in such high doses, which induce toxic effects. Opiates alone proved to be effective, but their practical use cannot be taken into consideration because of the danger of several side effects [Szolcsányi, J.: Neurogenic inflammation: reevaluation of axon reflex theory. In: Neurogenic Inflammation. P. Gepetti and P. Holzer (eds.), CRP Press, Boca Raton Fl. 35–44 (1996); Capsaicin and neurogenic inflammation: History and early findings. In: Antidromic vasodilataton and neurogenic inflammation. L. A. Chahl and J. Szolcsányi: Systemic anti-inflammatory effect induced by antidromic stimulation of the dorsal roots in the rat. Neuroscience Letters 212, 1–4 (1996)].

It had been proven in earlier studies that the pretreatment with somatostatin prevented the experimentally induced neurogenic inflammation, but because of its broad spectrum of activities (endocrine action, modulation of cardiovascular and gastrointestinal functions, influence on cognitive and behavioural processes) and its short half life, it cannot be taken into account from a therapeutical point of view.

It has been shown that somatostatin can be found in the peripheral endings of capsaicin-sensitive primary afferent neurons (CSPAN) and is liberated on the effect of stimulation. Capsaicin (8-methyl-N-vanillyl-6-nonene amide), the pungent substance of red pepper, selectively stimulates or, in high doses, selectively stimulates a subgroup of primary afferent neurons (small, dark nerve cells of type B). On the basis of this property, this subpopulation of neurons is recorded under the name "capsaicin-sensitive primary afferent neurons) (CSPAN) in the literature [Szolcsányi, J., Pórsz ász, R., Pethö, G.: Capsaicin and pharmacology of nociceptors. In: Peripheral neurons in nociception: physiopharmacological aspects. J. M. Besson, G. Gialbaud, I. Ollat (eds.), John Libbey, Eurotext, Paris 109–124 (1994); Maggi, C. A.: Tachykinins and calcitonin gene-related peptide (CGRP) as co-transmitters released from peripheral endings of sensory nerves. Progr. Neurobiol. 45, 1–98 (1995)]. Capsaicin-sensitive primary sensory neurons form about one half of the nerve cell population of sensory ganglions. This group includes the C-polymodal nociceptors amounting to about 60 to 70% of C-afferentation of the skin as well as the perivascular chemoceptive interoceptors of the mucous membranes (conjunctiva, airways, urogenital system, etc.) and visceral organs (heart, kidney, stomach etc.), which can be excited by chemical painstimuli (bradykinin, acids, capsaicin). A common property of these nociceptive afferents without unmedullated fibres or with a thin myelin sheath of A-delta fibre range is that, under the effect of stimuli, tachykinins (P substance, neurokinin A), calcitonin gene-related peptide (CGRP) [C. A. Maggi: Tachykinins and calcitonin gene related peptide (CGRP) as cotransmitters released from peripheral endings of sensory nerves. Progress in Neurobiology 45, 1–98 (1995)] and somatostatin are released from their peripheral endings. Tachykinins induce plasma extravasation and neurogenic inflammation on the venules whereas CGRP gives rise chiefly to vasodilatation of the arterioles and enhancement of microcirculation [L. A. Chahl: Antidromic vasodilatation and neurogenic inflammation. Pharmacol. Ther. 37, 275–300 (1988)]. Thus, the capsaicin-sensitive peptidergic sensory nerve endings and terminal varicosities equally provide both a nociceptive afferent function as well as an efferent function eliciting a local tissue response. They play an important role in the signalling of neuropathic or inflammatory as well as hot stimulus- or irritant-induced pains [Szolcsányi, J.: Actions of capsaicin on sensory receptors. In: Capsaicin in the Study of Pain, J. N. Wood (ed.), Academic Press, London 1–26 (1993)].

SUMMARY OF THE INVENTION

The aim of the invention is to develop pharmaceutical compositions, which are equally useful to inhibit both neurogenic and non-neurogenic inflammations as well as to alleviate pain.

DETAILED DESCRIPTION OF THE INVENTION

Accordingly, the present invention relates to pharmaceutical compositions possessing neurogenic or non-neurogenic anti-inflammatory as well as analgetic effects, and methods for using them.

The invention is based on the recognition that the above aim can be achieved by using the compounds of formulae (I) and (II), that is to say the development of neurogenic and non-neurogenic inflammations can be prevented and an alleviation of pain can be accomplished. This recognition is surprising since no family of compounds is known at present which, when used as a drug, could reliably prevent neurogenic inflammations. Although, as indicated above, somatostatin prevents the experimentally induced neurogenic inflammation, it cannot therapeutically be taken into consideration because of its broad spectrum of activities (endocrine effects, modulation of cardiovascular and gastrointestinal functions, influence of cognitive and behavioural processes) and short half life.

Thus, the invention relates to the use of peptide amides of formula (I), wherein $X_1$ means an aromatic D-amino acid group or a derivative thereof, ring-substituted by halogen or hydroxyl group; aminosuccinyl, D-2-naphthylalanyl, D-tetrahydroisoquinolinyl-carbonyl, glycyl or —NH—CH—(CO—$A_1$)—CH$_2$—CO— group, wherein
$A_1$ is an 1-indolinyl group;

$X_2$ stands for an aromatic amino acid group or a derivative thereof, ring-substituted by halogen or hydroxyl group; or tetrahydroisoquinolinyl-carbonyl or glycyl group;

$X_3$ means an aromatic D-amino acid group, D-pyridinoalanyl, glycyl or aminosuccinyl group;

$X_4$ represents threonyl, tryptophyl, glycyl or 2-naphthylalanyl group;

k is 0, 1, 2 or 3;

n is 0, 3 or 4;

$R_1$ stands for hydrogen or an $A_2$—CO— group, wherein $A_2$ is $C_{1-4}$ alkyl group;

$R_2$ means hydrogen, phenyl, p-hydroxyphenyl or carbonyl group;

$R_3$ stands for hydrogen, amino, guanidino or $A_3$—NH— group, wherein
$A_3$ means acetyl or trifluoroacetyl group;

$R_4$ stands for hydrogen, phenyl, p-hydroxyphenyl or amino group; or $R_2$ and $R_4$ together form a disulfide bridge or an acid amide moiety, or of oxaniloylhydrazone type peptoides of formula (II), wherein $Q_1$ means hydrogen, hydroxyl group, halogen, nitro group, amino group, $C_{1-4}$ alkyl or $C_{1-4}$ alkoxy group;

$Q_2$ stands for hydrogen, hydroxyl group, halogen or nitro group;

$Q_3$ means hydrogen, hydroxyl group, halogen, nitro group, —CF$_3$ group, $C_{1-4}$ alkyl or $C_{1-4}$ alkoxy group;

$Q_4$ and $Q_5$ each represent hydrogen, hydroxyl group, halogen, nitro group, —CF$_3$ group, $C_{1-4}$ alkyl or $C_{1-4}$ alkoxy group; or $C_{1-3}$ dialkylamino group, as well as the salts of these compounds for the preparation of pharmaceutical compositions possessing neurogenic or non-nenurogenic anti-inflammatory as well as analgetic effects.

The following compounds can preferably be used as active components: D-Phe-Cys-Tyr-D-Trp-Lys-Cys-Thr-NH$_2$ (TT-232), furthermore D-Phe-Cys-Tyr-D-Trp-Lys-Cys-Trp-NH$_2$ (VZ-924), β-Asp(indolinyl)-Cys-Tyr-D-Trp-Lys-Cys-Thr-NH$_2$ (VZ-927), D-Phe-Cys-Tyr-D-Trp-Gly-Cys-Thr-NH$_2$ (VZ-934), D-Phe-Cys-Tyr-Gly-Lys-Cys-Thr-NH$_2$ (VZ-1021), D-β-naphthylalanyl-Cys-Tyr-D-Trp-Lys-Cys-Thr-NH$_2$ (BAH-21), acetyl-D-Phe-Cys-Tyr-D-Trp-Lys-Cys-Thr-NH$_2$, D-Phe-Cys-Tyr-D-pyridinoalanyl-Lys-Cys-Thr-NH$_2$ (VZ 1034), Gly-Cys-Tyr-D-Trp-Lys-Cys-Thr-NH$_2$ (VZ-1017), D-Phe-Cys-Gly-D-Trp-Lys-Cys-Thr-NH$_2$ (VZ-1024), D-Phe-Cys-Tyr-D-Trp-Lys-Cys-Gly-NH$_2$ (VZ-1038), D-Phe-Cys-Tyr-D-Trp-Arg-Cys-Thr-NH$_2$ (VZ-1026), amino-succinyl-Cys-Tyr-D-Trp-Lys-Cys-Thr-NH$_2$ (VZ 927), D-Phe-Phe-Tyr-D-Trp-Lys-Phe-Thr-NH$_2$, D-Phe-Cys-Tyr-D-Trp-Lys-Cys-β-naphthyl-alanyl-NH$_2$ (BAH-52), D-Phe-Asp-Tyr-D-Trp-Lys-diaminopropionyl-Thr-NH$_2$ (EJ-48), D-Phe-Glu-Tyr-D-Trp-Lys-diaminopropionyl-Thr-NH$_2$ (EJ-47), D-tetrahydroisoquinolinyl-carbonyl-Cys-Tyr-D-Trp-Lys-Cys-Thr-NH$_2$ (BAH-21);

3'-nitrophenylamino-2-oxoacetyl-3",4"-dihydroxyphenyl-hydra-zone (HDL-2722), 4'-N,N-dimethylaminophenylamino-2-oxoacetyl-3",4"-dihydroxyphenyl-hidrazone (HDL-422), 3'-hydroxyphenylamino-2-oxoacetyl-3",4"-dihydroxyphenyl-hidrazone (HDL-622), 4'-ethoxyphenylamino-2-oxoacetyl-3",4"-dihydroxyphenyl-hidrazone (HDL-1322), 4'-ethoxyphenylamino-2-oxoacetyl-4"-N,N-dimethylamino-phenyl-hidrazone (HDL-1325), 4'-nitrophenylamino-2-oxoacetyl-3",4"-di-hydroxyphenyl-hidrazone (HDL-2222), 3'-nitrophenylamino-2-oxo-acetyl-3"-hydroxyphenyl-hydrazone (HDL-2734), 3'-nitrophenylamino-2-oxoacetyl-4"-hydroxyphenyl-hidrazone. (Signs in parentheses relate to the code names of the compounds.)

A common characteristic of the pharmaceutical compositions prepared by the process of invention is that they inhibit the neurogenic inflammation to a greater extent than natural somatostatin does and under conditions of use they are more stable than somatostatin. In contrast to somatostatin and other known somatostatin analogues, an other advantageous property of the compounds is that they are selective, do not induce endocrine effects and simulatenously they significantly inhibit the developing of inflammations and have a considerable analgetic action, too. This is of extraordinary importance since, in contrast to the compositions used until now, they are free of serious toxic effects during antiinflammatory and analgetic treatments.

The preparation of compounds of formula (I) is known from the Hungarian patent specification No. 207,104 and its equivalent U.S. Pat. No. 5,480,870. Preparation of compounds of formula (II) is known from the U.S. patent application Ser. Nos. 08/179,142 and 08/179,570 and from the Hungarian patent specification No. 214,061.

According to the invention, pharmaceutical compositions useful for the inhibition of neurogenic and non-neurogenic inflammations and for pain alleviation can be prepared by mixing the compounds of formula (I) or formula (II), the salts or metal complexes thereof with carriers and/or auxiliaries commonly used in the pharmaceutical industry, then transforming the mixture to a pharmaceutical composition.

The pharmaceutical composition may contain any therapeutically useful solvent (e.g. water, aqueous solution containing thioalcohol and/or polyalcohol such as polyethylene glycol and/or glycerol etc.); salts (e.g. sodium chloride for adjustment of the physiological osmotic pressure; iron, cobalt, zinc or copper chlorides and the like for supplementing trace elements); fillers and carriers (e.g. lactose, potato starch, talc, magnesium carbonate, calcium carbonate, waxes, vegetable oils, polyalcohols etc.); auxiliaries promoting dissolution (such as certain polar organic solvents, in the case of water usually ethanol, polyalcohols, most frequently polyethylene glycol or glycerol and/or complex forming agents, e.g. cyclodextrins, crown ethers, natural proteins, saponins and the like); tablet-disintegrating agents (artificial or natural polymers strongly swelling in water, e.g. carboxymethylcellulose); complex-forming agents usually employed in retard compositions (such as water-insoluble or slightly soluble cyclodextrin derivatives, artificial and natural polymers, crown ethers and the like); pH-adjusting compounds such as mineral or organic buffers; taste-improving agents (cyclodextrins and/or crown ethers); and flavouring agents (beet sugar, fruit sugar or grape sugar, saccharin, invert sugar etc.); antioxidants (e.g. vitamin C) as well as substances promoting the effectiveness of the action of compounds of formulae (I) and (II).

The compounds of formulae (I) and (II) are useful also in aerosol compositions aimed at the absorption through the skin surface or lungs.

For the preparation of tablets, dragées or hard gelatine capsules e.g. lactose, maize, wheat or potato starches, talc, magnesium carbonate, magnesium stearate, calcium carbonate, stearic acid and its salts etc. can be used as carriers. For the preparation of soft gelatine capsules e.g. vegetable oils, fats, waxes, or polyalcohols with an appropriate density can be used as carriers. For the preparation of solutions and syrups e.g. water, polyalcohols such as polyethylene glycol and glycerol, beet sugar, grape sugar etc. can be employed as carriers. Parenteral compositions may contain water, alcohol, polyalcohols or vegetable oils as carriers. Suppositories may contain e.g. oils, waxes, fats or polyalcohols of appropriate density as carriers.

The pharmaceutical compositions prepared by the process according to the invention are suitably used in a daily dose of 0.5 to 5000, preferably 1 to 500, more preferably 5 to 150 μg/kg of body weight.

The main advantages of the invention are as follows:
a) It provides to diminish inflammations of both neurogenic and non-neurogenic origin with simultaneous exertion of an analgetic effect.
b) The somatostatin analogues used in the invention are more slowly decomposed under in vivo conditions than the natural compound; therefore, their action is more durable.
c) The compounds used according to the invention do not induce endocrine effects which would appear as severe side effects during the antiinflammatory or analgetic treatment.

The activity of the pharmaceutical compositions prepared according to the invention has been proven by the following studies.

1. Study of the Antiinflammatory Action 1.1. Investigation of the Neurogenic Antiinflammatory Effect Thirty minutes after acute bilateral denervation of the lower limbs (transsection of the saphenous and sciatic nerves), 50 mg/kg of Evans blue dye was administered to the tail vein of nembutal-anaesthetized (pentobarbital, 40 mg/kg i.p.) Wistar rats (150–220 g body weight; 5 to 7 animals in each group). The pretreated animals received simultaneously and intraperitoneally various doses of somatostatin (SS), octreotide, TT-232, VZ-927, VZ-1021 or VZ-934, respectively. Ten minutes later, both feet of the rats were painted with mustard oil of 1%. The mustard oil induces a so-called neurogenic inflammation by the selective stimulation of the peripheral endings of CSPAN's and by releasing the mediators being present therein (chiefly tachykinins and CGRP); this neurogenic inflammation appears as a vasodilatation in the area of arterioles and in the form of a plasma extravasation at the venular side. Since the dye Evans blue is bound to serum albumin in the vascular bed, its precipitation and accumulation in the upper skin surface of foot are proportional to the extent of plasma extravasation. Thus, the quantitative determination of intensity of the inflammation becomes possible. After the painting with mustard oil, the animals were bled, the foot dorsum skins were cut out and their weights were determined. The amount of dye extracted during 72 hours of incubation in formamide was determined at 620 nm on a spectrophotometer (Spectromon 195). The amount (expressed as μg) of the extravasated Evans blue related to one g of wet tissue was calculated by means of the following formula:

$$\text{Evans blue } (\mu g/g) = E \times V \times k / m$$

wherein

E is the light absorption of the solution,

V means the volume (ml) of the solution, m is the weight (mg) of the skin cut out from the foot dorsum skin; and k is a constant determined on the basis of a dilution series, which is characteristic of the dye solution.

Figure 1:
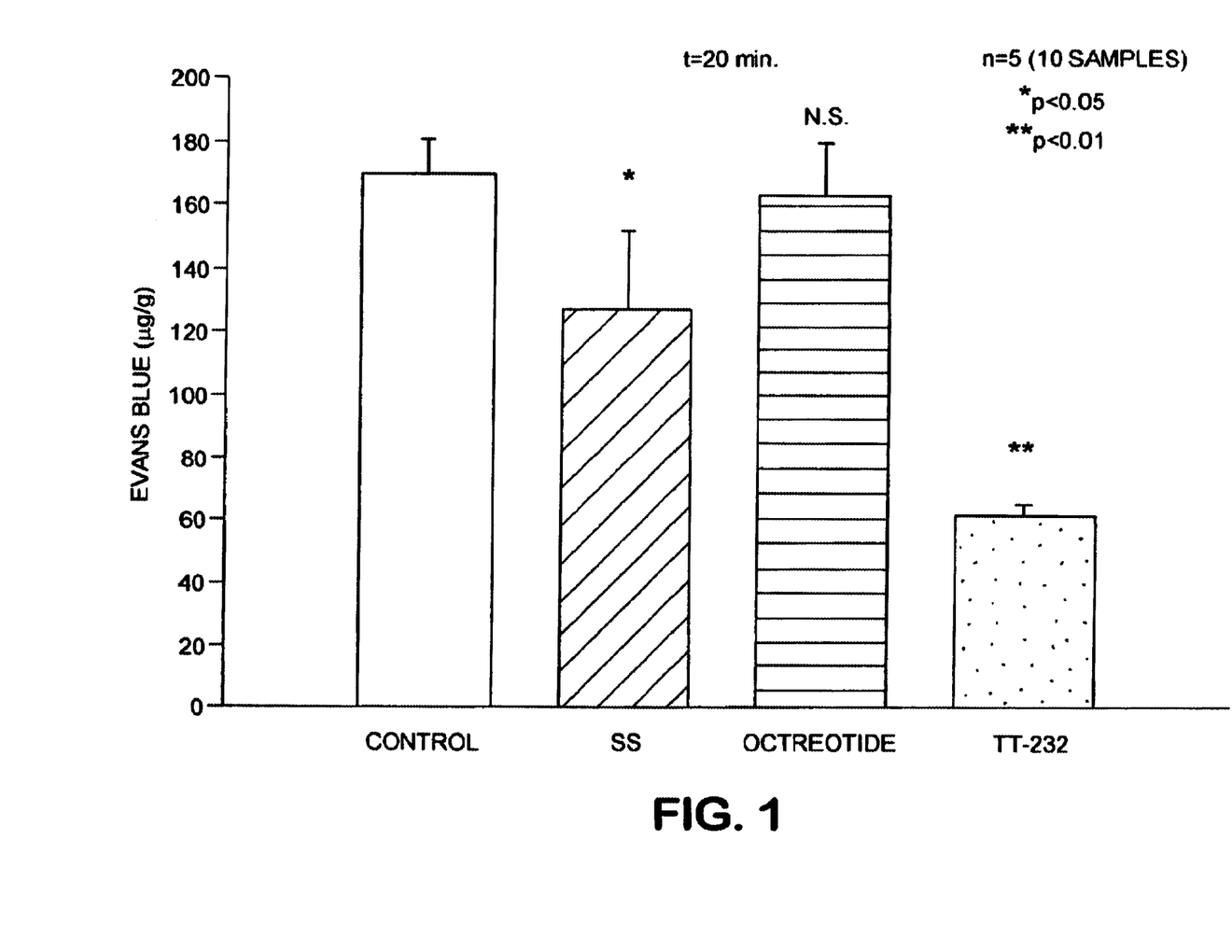

The results are summarized in Table 1 and illustrated in FIG. 1. It can be seen from Table 1 that the heptapeptide analogue representing the compounds of formula (I) (TT-232, VZ-927, VZ-924, VZ-1021, VZ-934) significantly inhibited the mustard oil-induced neurogenic inflammation in a dose of 20 μg/kg 20 minutes after i.p. administration; whereas octreotide, an octapeptide somatostatin analogue known from the literature and used in the clinical practice, proved to be inactive.

Figure 2:
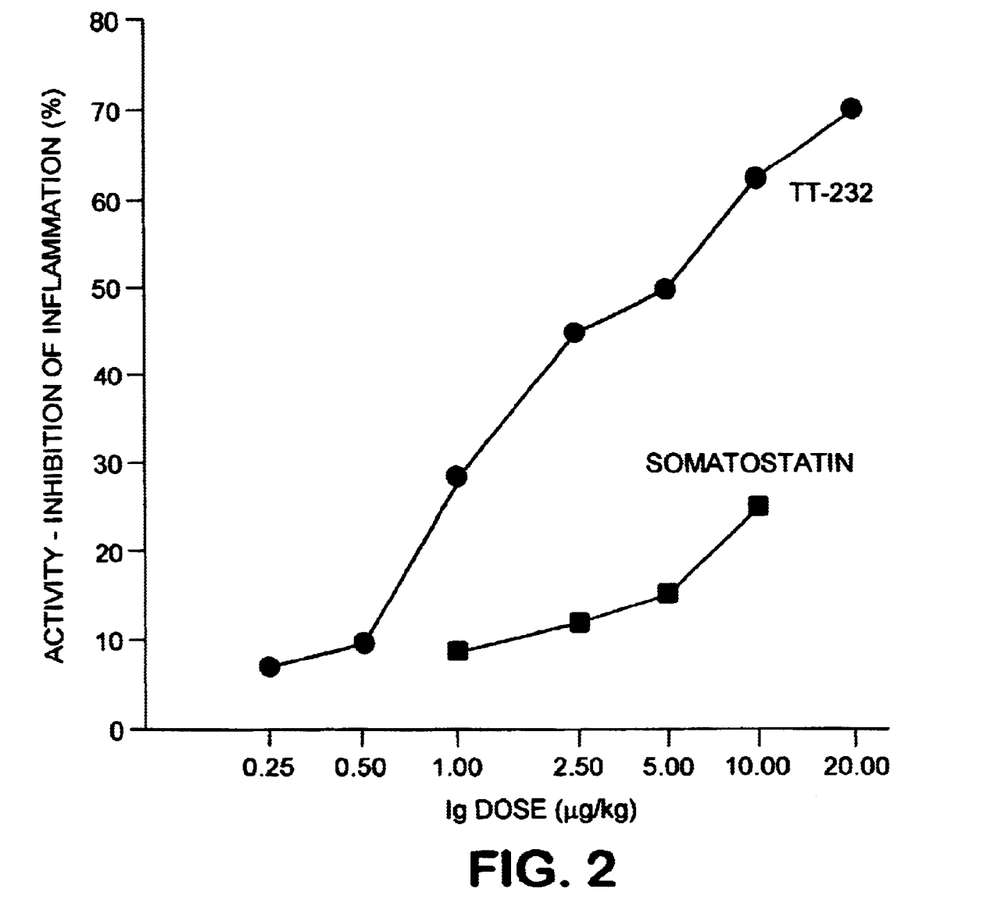
Figure 2A:
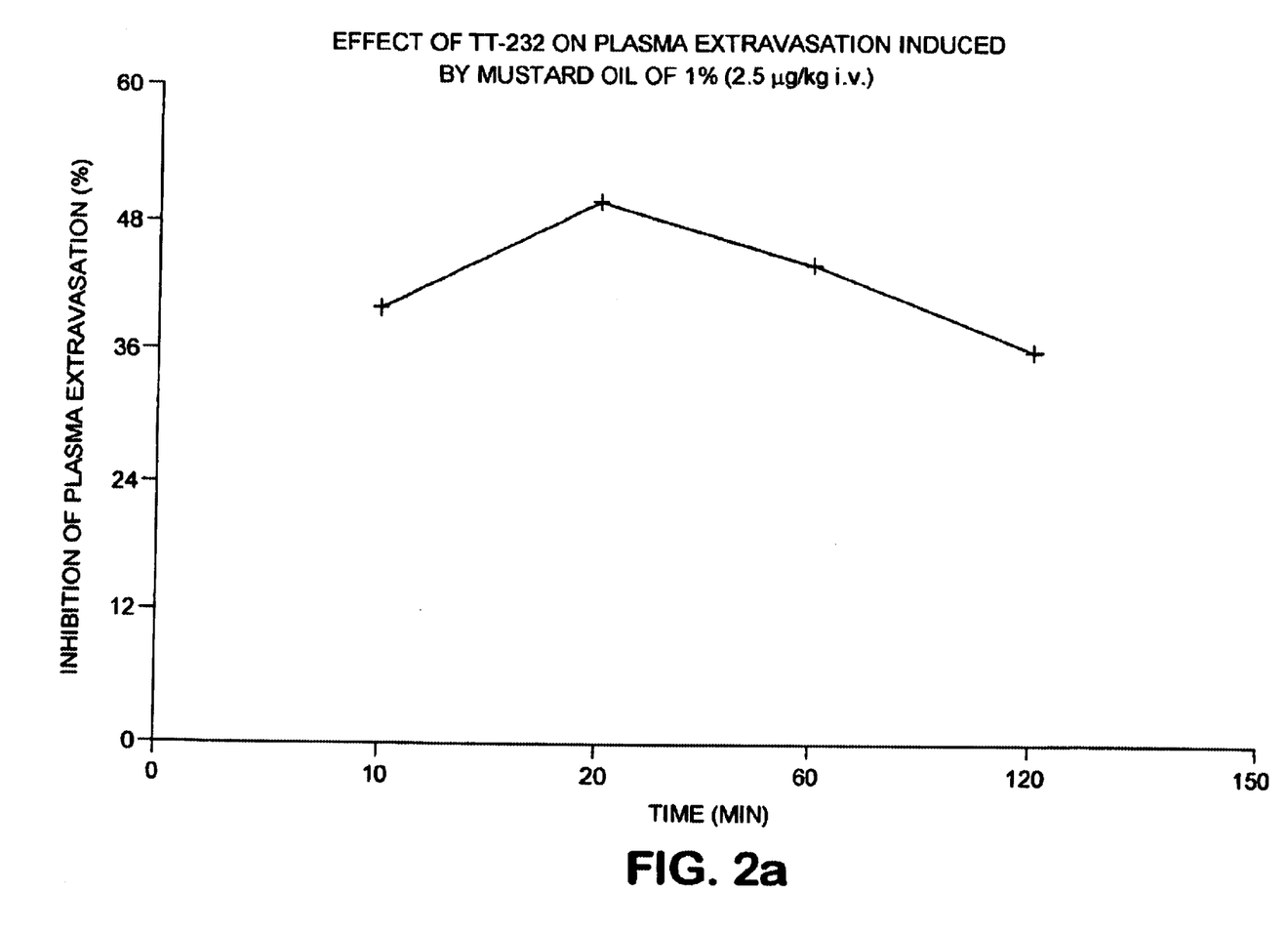

FIG. 2 shows the dose/effect relation. It can be seen that the highest antiinflammatory effect elicited by TT-232 is about the double of the highest effect, which can be induced by somatostatin. On the basis of an equipotent dose ratio TT-232 is active in about a 8-times lower dose; therefore, TT-232 is a more advantageous antiinflammatory compound than somatostatin both from the view-point of intrinsic activity as well as affinity. FIG. 2.a shows that the inhibition of inflammation elicited by an intravenous dose of 2.5 μg/kg was found to be 35% even 2 hours after administration.

The active substance HDL 2722 (50 μg) resulted in a 62% inhibition of the 1% mustard oil-induced neurogenic inflammation (plasma extravasation).

TABLE 1

Effects of somatostatin analogues on the 1% mustard oil-induced neurogenic inflammation

|  | Control | Somatostatin | Octreotide | TT-232 | VZ-927 | VZ-924 | VZ-1021 | YZ-934 |
|---|---|---|---|---|---|---|---|---|
| Evans blue extravasation | 169.525 SEM:* 10.81 | 127.39 SEM: 24.32 p = 3.76 E-2 | 162.826 SEM: 16.921 p = 0.186 | 61.68 SEM: 3.72 p = 1.82 E-4 | 67.07 SEM: 6.75 p = 2.73 E-5 | 75.26 SEM: 6.23 p = 4.4 E-4 | 76.72 SEM: 8.33 p = 7.69 E-4 | 93.7 SEM: 15.07 p = 9.1 E-3 |
| Decrease % |  | 24.85 | 3.952 | 63.616 | 60.44 | 55.62 | 54.72 | 44.7 |

*SEM: standard error of the mean

1.2. Investigation of the Inhibitory Effect on the Non-neurogenic, So-called Clearly Chemical Inflammation

1.2.1. Inhibition of the Non-neurogenic Inflammation Elicited by Dextran

This test is based on the fact that a non-neurogenic, so-called clearly chemical inflammation can be induced by chemical excitation (e.g. by dextran, carrageenin, formalin) on a chronically denervated body area at least 5 days following the transsection of the nerve. These chemical agents release inflammation-inducing substances (histamine, bradykinin, PAF, prostaglandins and leucotrienes) from immunocytes, chiefly from mast cells.

Dextran solution (0.1 ml, 0.5%) is administered into both feet, underneath the plantar skin of Wistar rats (5 to 7 animals in each group) anaesthetized by nembutal (40 mg/kg i.v.) 5 days after bilateral denervation (transsection of the saphenous and sciatic nerves) of the lower limbs. The pretreated animals received somatostatin (SS), ocreotide or TT-232 (10 μg/kg i.p.) 10 minutes earlier. Before the administration of dextran (0 minute value), then after 10, 20 and 30 minutes, respectively, the swelling of the feet was measured by using a plethysmometer (Ugo Basil). Dextran elicits the so-called clearly chemical inflammation in the feet deprived of nerve supply (innervation) through the transmitters released from the mast cells.

Figure 3:
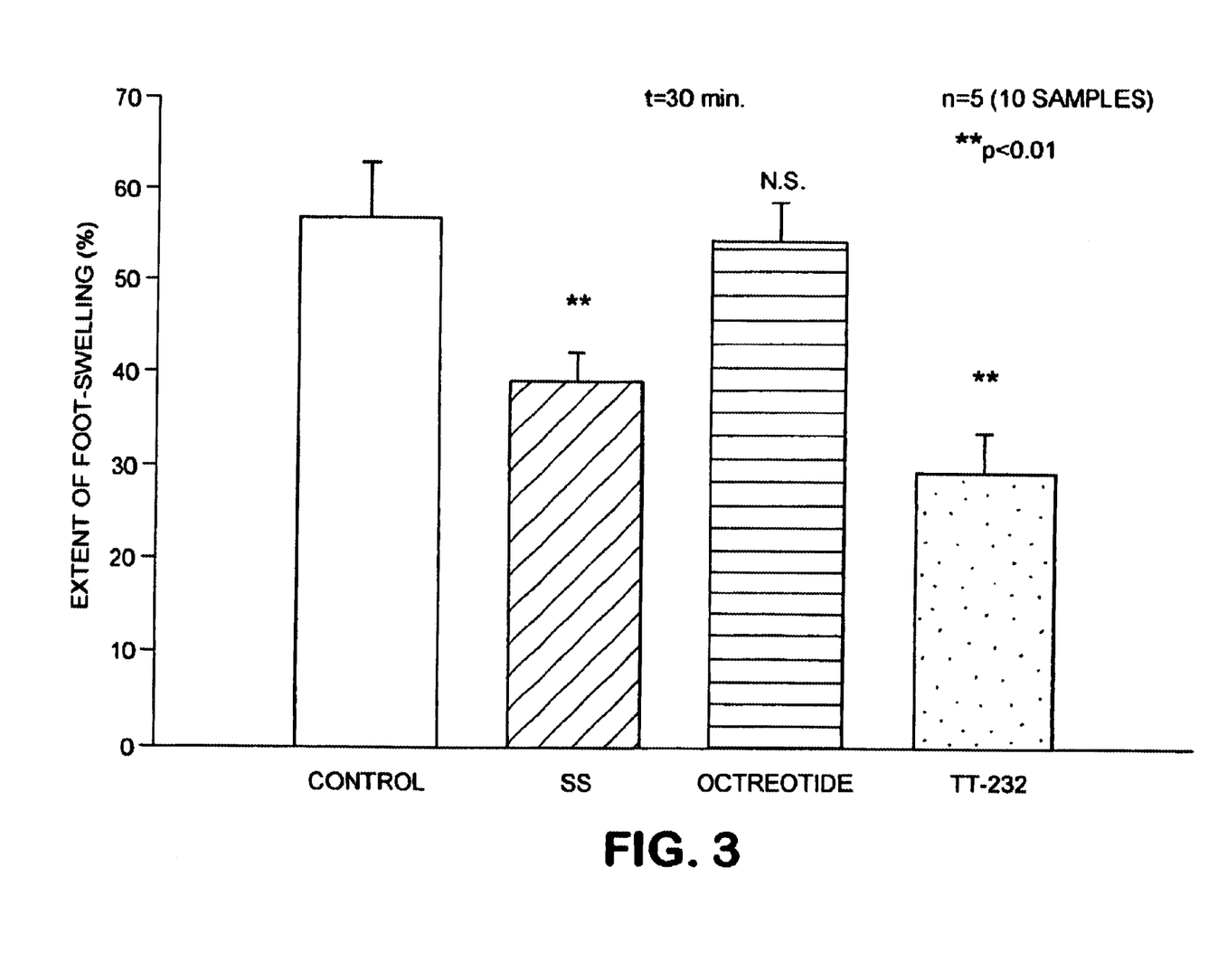

The results are summarized in Table 2 and illustrated in FIG. 3. It can be observed that the pretreatment by TT-232 (10 μg/kg) significantly prevented the dextran-induced non-neurogenic inflammation even 40 minutes following the pretreatment. Octreotide was found to be completely inactive in the same dose.

TABLE 2

Effect of somatostatin analogues on the 0.5% dextran-induced non-neurogenic inflammation

|  | Control | Somatostatin | Octreotide | TT-232 |
|---|---|---|---|---|
| 10 minutes foot swelling % | 32.97 SEM: 2.8 | 19.5 SEM: 3.37 p = 8.88 E-3 | 31.36 SEM: 3.96 p = 0.67 | 24.4 SEM: 5.065 p = 0.048 |
| 20 minutes foot swelling % | 49.695 SEM: 3.27 | 34.2 SEM: 4.35 p = 9.828 E-4 | 47.7 SEM: 5.56 p = 0.343 | 34.39 SEM: 1.6 p = 4.69 E-4 |
| 30 minutes foot swelling % | 56.68 SEM: 3.69 | 39.13 SEM: 3.14 p = 1.485 E-4 | 54.8 SEM: 4.55 p = 0.127 | 29.43 SEM: 4.405 p = 3.012 E-4 |

The experiment described above was repeated in such a way that the antiinflammatory effect of TT-232 was compared to two other well known antiinflammatory substances (diclofenac and meloxicam) of non-peptide structure. A dose/effect ratio was determined for each substance. The results are summarized in Table 2.a. It can be seen that, in comparison with the control results corresponding to the invidual substances, TT-232 prevented the foot-swelling more effectively in every case whereas its concentration was only a thousandth part of that of either other active substance.

1.2.2. Inhibition of the Bradykinin-induced Non-neurogenic Inflammation

After chronic denervation (see 1.2.1.), each group of 5 rats received various doses (1, 2.5, 5, 10 or 20 μg, respectively, i.v.) of TT-232 and simultaneously Evans blue (50 mg/kg i.v.). Ten minutes later, bradykinin was injected underneath the plantar skin of the lower limbs of the rats. After 15 minutes the animals were bled and the amount of the extravasated Evans blue (expressed as μg/kg related to the wet tissue) was determined as.described above (1.1.).

The results are summarized in Table 2.b).

TABLE 2.b

Effect of TT-232 on the bradykinin-induced non-neurogenic inflammation (Evans blue extravasation)

| Control | TT-232 ($\mu$g/kg) | | | | |
|---|---|---|---|---|---|
| (buffer) | 1 | 2.5 | 5 | 10 | 20 |
| 127.35 ± 7.11 | 98.21 ± 7.44<br>p = 0.02 | 85.02 ± 7.33<br>p = 0.002 | 81.95 ± 7.64<br>p = 0.001 | 86.31 ± 8.74<br>p = 0.006 | 77.4 ± 4.59<br>p = 0.0001 |

TABLE 2.a

Effect of TT-232, diclofenac and meloxicam on the non-neurogenic inflammation induced by 0.5% dextran (foot swelling %)

| | 10 minutes | 20 minutes | 30 minutes |
|---|---|---|---|
| TT-232 | | | |
| Control 1 (buffer) | 27.57 ± 4.79 | 49.79 ± 4.55 | 64.22 ± 3.99 |
| 0.5 $\mu$g/kg | 27.63 ± 3.5<br>p = 0.96 | 39.94 ± 3.07<br>p = 0.16 | 41.33 ± 5.95<br>p = 0.01 |
| 1.0 $\mu$g/kg | 20.51 ± 2.92<br>p = 0.17 | 38.07 ± 3.12<br>p = 0.048 | 44.32 ± 3.18<br>p = 0.0038 |
| 2.5 $\mu$g/kg | 20.54 ± 5.16<br>p = 0.15 | 33.02 ± 4.46<br>p = 0.024 | 39.59 ± 4.76<br>p = 0.007 |
| 5.0 $\mu$g/kg | 17.29 ± 3.13<br>p = 0.047 | 27.81 ± 2.39<br>p = 0.001 | 35.95 ± 2.97<br>p = 0.001 |
| 10 $\mu$g/kg | 17.60 ± 2.05<br>p = 0.04 | 27.59 ± 2.5<br>p = 0.002 | 36.40 ± 1.71<br>p = 0.0007 |
| 20 $\mu$g/kg | 19.56 ± 1.71<br>p = 0.08 | 29.73 ± 1.7<br>p = 0.003 | 37.67 ± 2.33<br>p = 0.001 |
| Diclofenac | | | |
| Control 2 (physiol. saline) | 34.52 ± 2.73 | 56.65 ± 3.05 | 64.60 ± 2.83 |
| 5 mg/kg | 28.98 ± 1.85<br>p = 0.04 | 48.73 ± 4.84<br>p = 0.38 | 53.07 ± 3.95<br>p = 0.053 |
| 10 mg/kg | 24.35 ± 3.31<br>p = 0.051 | 35.20 ± 2.92<br>p = 0.0005 | 42.61 ± 3.55<br>p = 0.001 |
| 20 mg/kg | 21.87 ± 2.84<br>p = 0.009 | 31.10 ± 2.36<br>p = 0.00014 | 33.90 ± 2.23<br>p = 0.0000873 |
| 30 mg/kg | 26.02 ± 1.79<br>p = 0.017 | 35.36 ± 2.79<br>p = 0.0006 | 40.20 ± 1.73<br>p = 0.0002 |
| Meloxicam | | | |
| Control 3 (placebo) | 40.31 ± 4.24 | 56.07 ± 4.32 | 68.90 ± 4.9 |
| 0.2 mg/kg | 27.60 ± 3.56<br>p = 0.05 | 39.99 ± 3.65<br>p = 0.01 | 45.81 ± 2.9<br>p = 0.001 |
| 0.5 mg/kg | 27.24 ± 3.56<br>p = 0.01 | 38.86 ± 2.86<br>p = 0.004 | 44.92 ± 2.99<br>p = 0.0003 |
| 1 mg/kg | 24.34 ± 2.57<br>p = 0.007 | 36.46 ± 3.44<br>p = 0.004 | 46.63 ± 3.2<br>p = 0.002 |
| 10 mg/kg | 20.39 ± 2.26<br>p = 0.002 | 33.36 ± 1.85<br>p = 0.001 | 39.34 ± 3.75<br>p = 0.0002 |

2. Study of the Analgetic Action 2.1. Investigation of the Analgetic Action through the Vegetative Reflex Responses of Anaesthetized Animals This test is based on the synchronous registration of several components of so-called pseudoaffective reflex responses, which can be induced on animals by pain-producing stimuli [Lim, R. K. S.: J. Comp. Neurol 118, 269–294 (1962)] under urethane anaesthesia.

A significant blood pressure increase of 45 mmHg as an average pressor response, heart rate increase of 85 (as an average) and hyperpnoea (the number of respirations increases by 61 per minute as an average) can be observed in control animals on the effect of strong chemonociceptive stimuli (painting of the lower limbs with 1% mustard oil or dropping a capsaicin solution of 100 $\mu$g/ml concentration into the eye) under urethane anaesthesia.

The blood pressure, heart rate and respiration of intact Wistar rats (5 to 7 animals in each group, with a body weight of 250 to 350 g) were continuously registered for 40 minutes through an arterial cannula as well as double ramifying trachea cannula. Ten minutes before beginning the measurement, the pretreated animals received intraperitoneally 10 $\mu$g/kg of somatostatin (SS), octreotide or TT-232, respectively. Both lower limbs of the animals were painted with mustard oil in the $3^{rd}$ minute and capsaicin solution was dropped into their eyes in the $23^{rd}$ minute. The vegetative responses given on these nociceptive stimuli were evaluated by using a specific computer program.

Figure 4:
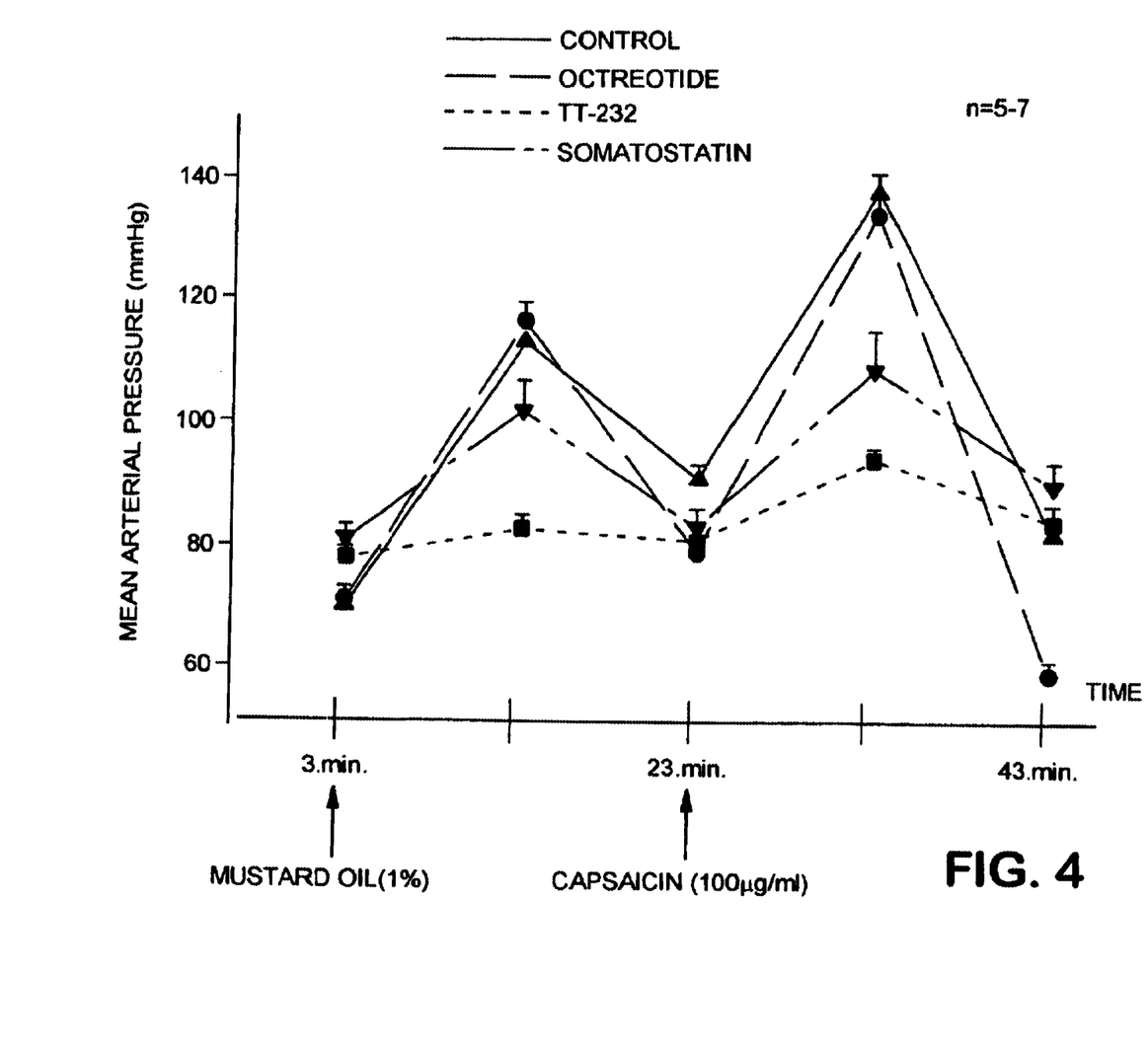
Figure 5:
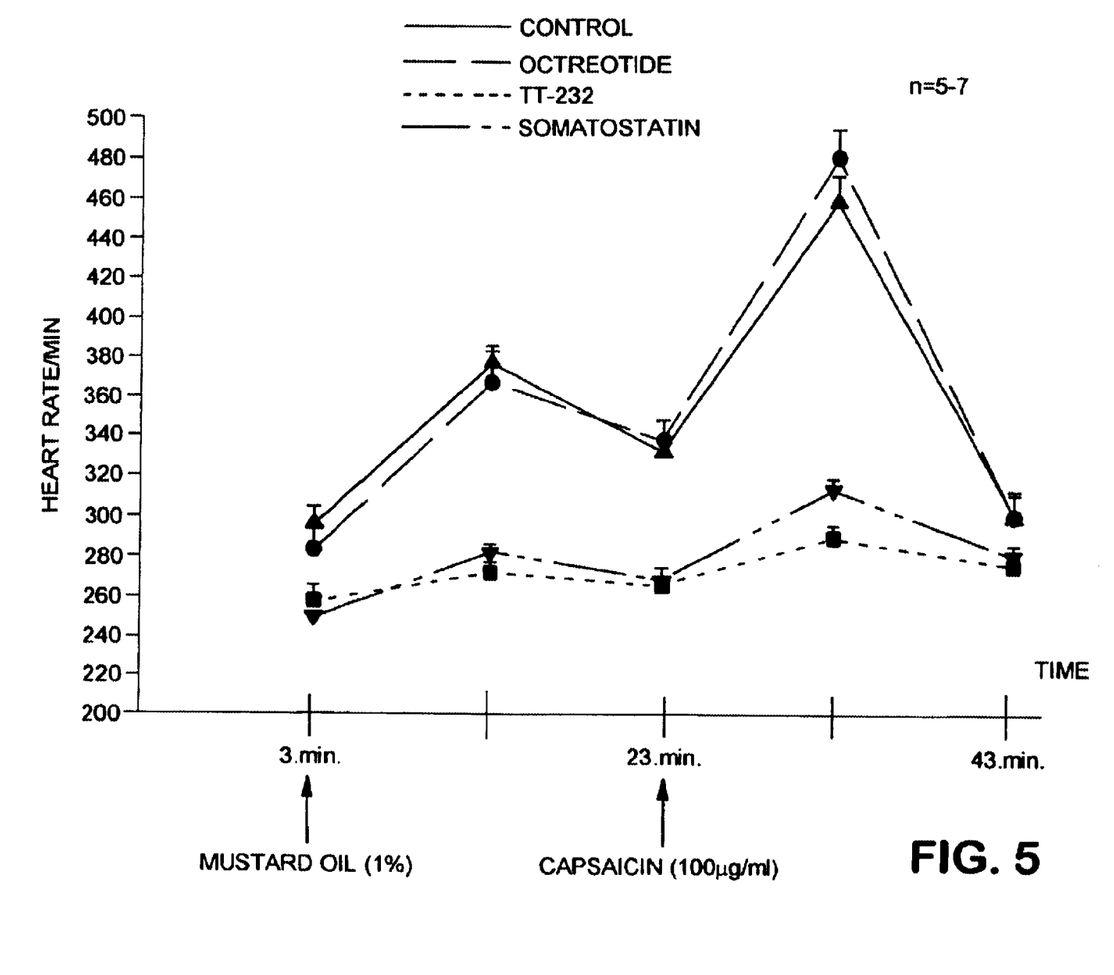
Figure 6:
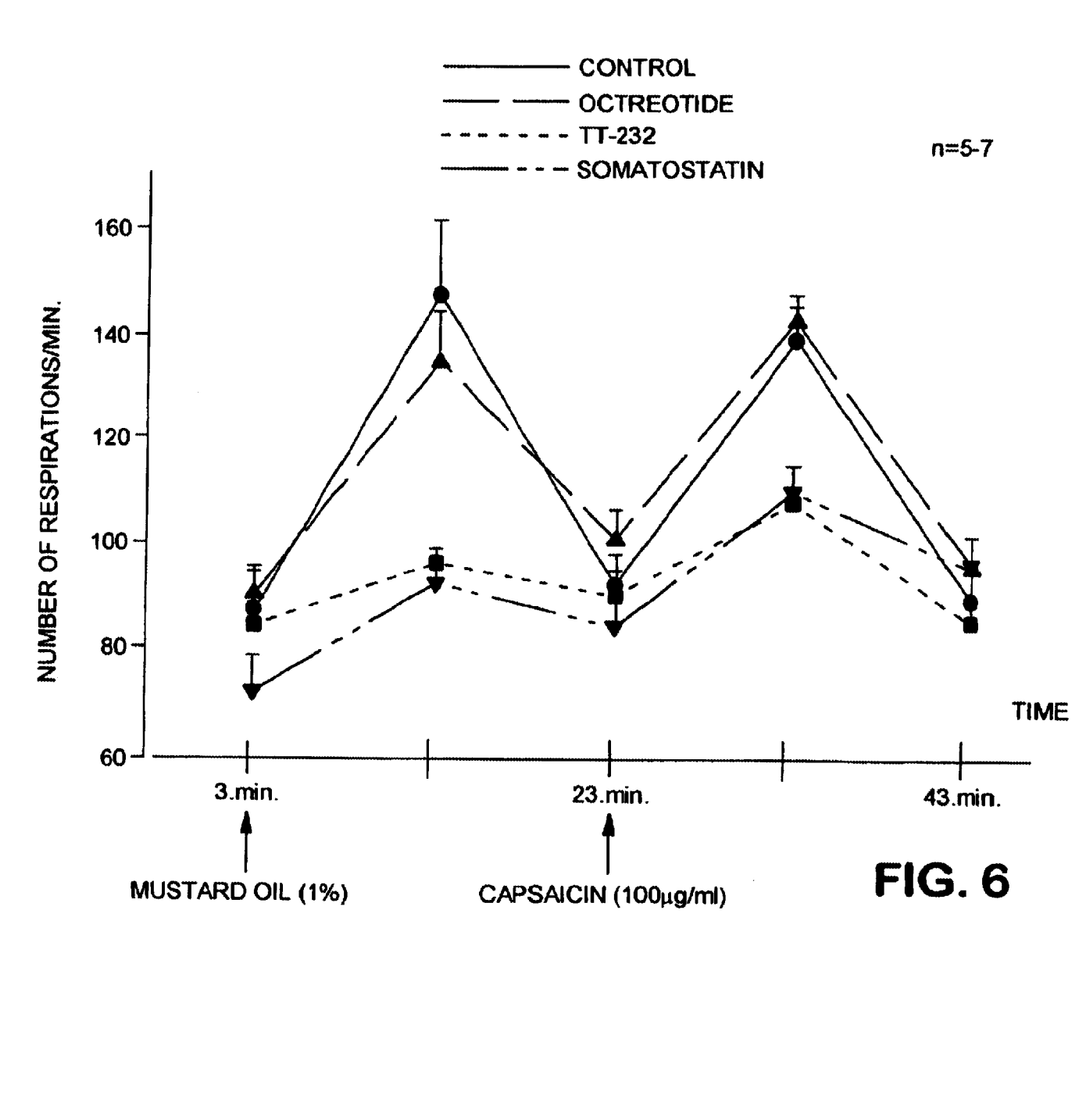

Our results are shown in Tables 3 and 4 as well as in FIGS. 4, 5 and 6. It can be seen from the results that a significant blood pressure elevation, tachycardia and increase in the respiration rate occurred in the control animals under effect of mustard oil or capsaicin. A pretreatment by TT-232 (10 $\mu$g/kg i.p., 10 minutes before the use of mustard oil) provided practically complete protection against this pseudoeffective reflex triad elicited by mustard oil and capsaicin, whereas octreotide proved to be completely inactive.

TABLE 3

Vegetative reflex responses after painting the feet by mustard oil

| | Control | Somatostatin | TT-232 | Octreotide |
|---|---|---|---|---|
| Increase in mean arterial pressure | 45.4<br>SEM: 3.059 | 21<br>SEM: 4.25<br>p = 0.023 | 4.86<br>SEM: 2.17<br>p = 0.00121 | 43.2<br>SEM: 6.24<br>p = 0.835 |
| Increase in heart rate | 84.8<br>SEM: 15.63 | 22.2<br>SEM: 3.9<br>p = 0.0099 | 13.71<br>SEM: 4.8<br>p = 0.0016 | 81.2<br>SEM: 8.27<br>p = 0.89 |
| Increase in respiration rate | 60.75<br>SEM: 14.01 | 20.2<br>SEM: 3.2<br>p = 0.0385 | 12<br>SEM: 2.91<br>p = 0.0029 | 45<br>SEM: 9.66<br>p = 0.43 |

TABLE 4

Vegetative reflex responses after dropping capsaicin solution into the eye

| | Control | Somatostatin | TT-232 | Octreotide |
|---|---|---|---|---|
| Increase in mean arterial pressure | 55<br>SEM: 3.605 | 25.6<br>SEM: 6.47<br>p = 0.0465 | 13<br>SEM: 1.476<br>p = 0.000675 | 47.13<br>SEM: 3.107<br>p = 0.114 |
| Increase in heart rate | 143<br>SEM: 13.57 | 27.4<br>SEM: 5.41<br>p = 0.0016 | 22.88<br>SEM: 6.4<br>p = 0.00076 | 127<br>SEM: 13.34<br>p = 0.87 |
| Increase in respiration rate | 47.5<br>SEM: 6.19 | 26<br>SEM: 4.52<br>p = 0.0082 | 17.85<br>SEM: 2.94<br>p = 0.0051 | 42<br>SEM: 4.93<br>p = 0.68 |

2.2. Investigation of the Analgetic Action by Measurement of the Mechanical Nociceptive Threshold Value The mechanical nociceptive threshold was investigated by using the Randall-Selitto test (Ugo Basil equipment) on unanaesthetized animals. Before the beginning of the experiment, the animals were tested several times to provide their adaptation to the experimental conditions. The animals received TT-232 in various concentrations (1.25, 2.5, 5, 10 μg i.v.) and after 15 minutes, carrageenin (0.1 ml of 1% solution) was injected into the plantar skin of the lower limbs of the animals. The increase in the nociceptive threshold, i.e. the analgetic effect, was found to be 30, 37, 50, or 60%, respectively, at 30 minutes after administration of carrageenin.

3. The in vitro Inhibition of the Release of "Sensory" Neuropeptides Releasing from the Trachea of Rats After bleeding out, the tracheas of two rats each were removed, placed into an organ bath (1.8 ml) and Krebs solution saturated with oxygen (95% of oxygen and 5% of carbon dioxide) was bubbled through it at 37° C. for 60 minutes (with a rate of 1 ml/min). After stopping the flow, the bath solution was changed 3 times (pre-stimulated—stimulated—post-stimulated) for 8 minutes. The release of sensory neuropeptides from the tissue samples was induced by electric (40 V, 0.1 ms, 10 Hz, 120 s) and chemical ($10^{-7}$ M of capsaicin) stimulation, in the presence or absence of TT-232 (200 nM, 500 nM). The fractions were collected in ice-cold tubes; the wet weights of tracheas were measured. The concentrations of substance P (SP), calcitonin gene-related peptide (CGRP) and somatostatin (SOM) were determined by using a specific radioimmunoassay (RIA) developed in our laboratory and expressed as the amount of peptide released from one g of tissue. The limits of measurements were: 2 fmol/tube for SP; 1 fmol/tube for CGRP; and 2 fmol/tube for SOM [Németh, J.: Acta Physiol. Hung. 84, 313–315 (1996); Helyes, Zs.: Br. J. Pharmacol. 121, 613–615 (1997)].

The amounts of SP (6 fmol/mg), CGRP (0.69 fmol/mg) and SOM (0.51 fmol/mg), respectively, released under the effect of electrical stimulation were decreased by 500 nm TT-232 to 3.8 fmol/mg of SP, 0.36 fmol/mg of CGRP and 0.39 fmol/mg of SOM, which represent an inhibition of 36, 48 and 42%, respectively. 500 nM TT-232 very significantly diminished the capsaicin-induced SP and SOM releases (79% and 74%, respectively); this inhibition was lower (27%) in the case of CGRP. TT-232 (200 nM) decreased by 44% the capsaicin-induced SP release and by 48% the SOM release, respectively. The basal, non-stimulated release of the neuropeptides was not affected by TT-232.

What is claimed is:

1. A method of inhibiting pain associated with neurogenic and non-neurogenic inflammations, which comprises treating a host with an effective amount of a compound of formula (II)

(II)

wherein
  $Q_1$ is hydrogen, hydroxyl, halogen, nitro, amino, $C_{1-4}$ alkyl or $C_{1-4}$ alkoxy;
  $Q_2$ is hydrogen, hydroxyl, halogen or nitro;
  $Q_3$ is hydrogen, hydroxyl, halogen, nitro, —$CF_3$, $C_{1-4}$ alkyl or $C_{1-4}$ alkoxy;
  $Q_4$ and $Q_5$ each are hydrogen, hydroxyl, halogen, nitro, —$CF_3$, $C_{1-4}$ alkyl, $C_{1-4}$ alkoxy or $C_{1-3}$ dialkylamino.

2. The method defined in claim 1, wherein the compound administered is 3'-nitrophenylamino-2-oxoacetyl-3",4"-dihydroxyphenylhydrazone.

3. The method defined in claim 1, wherein the compound administered is selected from the group consisting of 3'-nitrophenylamino-2-oxoacetyl-3",4"-dihydroxyphenylhydrazone, 4'-N,N-dimethylaminophenylamino-2-oxoacetyl-3",4"-dihydroxyphenylhydrazone, 3'-hydroxyphenylamino-2-oxoacetyl-3",4"-dihydroxyphenylhydrazone, 4'ethoxyphenylamino-2-oxoacetyl-3",4"-dihydroxyphenyl-hydrazone, 4'-ethoxyphenylamino-2-oxoacetyl-4"-N,N-dimentylaminophenylhydrazone, 4'-nitrophenylamino-2-oxoacetyl-3",4"-dihydroxyphenyl-hydrazone, 3'-nitrophenylamino-2-oxoacetyl-3"-hydroxyphenyl-hydrazone, 3'-nitrophenylamino-2-oxoacetyl-4"-hydroxyphenyl-hydrazone or a combination thereof.

4. The method defined in claim 1 for the inhibition of neurogenic and non-neurogenic inflammations.

5. The method defined in claim 4, wherein the compound administered is 3'-nitrophenylamino-2-oxoacetyl-3",4"-dihydrophenylhydrazone.

* * * * *